United States Patent
Miyama et al.

(10) Patent No.: US 8,394,024 B2
(45) Date of Patent: Mar. 12, 2013

(54) ULTRASOUND DIAGNOSTIC APPARATUS AND METHOD FOR TRACING MOVEMENT OF TISSUE

(75) Inventors: Koji Miyama, Tokyo (JP); Masafumi Ogasawara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 13/283,302

(22) Filed: Oct. 27, 2011

(65) Prior Publication Data

US 2012/0108970 A1 May 3, 2012

(30) Foreign Application Priority Data

Oct. 27, 2010 (JP) ................................. 2010-241317

(51) Int. Cl.
*A61B 8/00* (2006.01)
(52) U.S. Cl. ........................ 600/437; 600/443
(58) Field of Classification Search .......... 600/437–469; 382/128–132
See application file for complete search history.

(56) References Cited

U.S. PATENT DOCUMENTS

| | | | | |
|---|---|---|---|---|
| 5,622,174 | A * | 4/1997 | Yamazaki | 600/441 |
| 5,860,931 | A * | 1/1999 | Chandler | 600/458 |
| 6,258,031 | B1 * | 7/2001 | Sunagawa et al. | 600/443 |
| 6,447,453 | B1 * | 9/2002 | Roundhill et al. | 600/443 |
| 6,638,221 | B2 * | 10/2003 | Abe et al. | 600/437 |
| 6,770,034 | B2 * | 8/2004 | Sunagawa et al. | 600/443 |
| 6,884,216 | B2 * | 4/2005 | Abe et al. | 600/440 |
| 7,022,077 | B2 * | 4/2006 | Mourad et al. | 600/449 |
| 7,455,640 | B2 * | 11/2008 | Suzuki et al. | 600/437 |
| 7,575,551 | B2 * | 8/2009 | Watanabe et al. | 600/443 |
| 7,583,828 | B2 | 9/2009 | Hall et al. | |
| 7,815,574 | B2 * | 10/2010 | Mourad et al. | 600/453 |
| 8,167,802 | B2 * | 5/2012 | Baba et al. | 600/437 |
| 2002/0072672 | A1 * | 6/2002 | Roundhill et al. | 600/450 |
| 2003/0009101 | A1 * | 1/2003 | Sunagawa et al. | 600/437 |
| 2003/0083578 | A1 * | 5/2003 | Abe et al. | 600/447 |
| 2004/0059220 | A1 * | 3/2004 | Mourad et al. | 600/442 |

(Continued)

FOREIGN PATENT DOCUMENTS

| | | |
|---|---|---|
| JP | 06259560 | 9/1994 |
| JP | 2001120549 | 5/2001 |

(Continued)

OTHER PUBLICATIONS

Japanese Office Action; Application No. 2010-241317; dated Oct. 1, 2012; pp. 4.

*Primary Examiner* — Sanjay Cattungal
(74) *Attorney, Agent, or Firm* — Armstrong Teasdale LLP (57) ABSTRACT

An ultrasound diagnostic apparatus includes a transmitting and receiving unit that transmits an ultrasound wave to a target object in sequence and receives the ultrasound wave as ultrasound data reflected from the target object including a blood vessel. A first memory unit stores the received ultrasound data. An image generation unit generates an ultrasound image as a sectional image of the blood vessel. A display unit displays the ultrasound image. A region of interest (ROI) setting unit sets a plurality of ROIs on an inner wall and an outer wall of the blood vessel at a designated time. The ROIs are generated from the ultrasound data. A tracing unit traces movement of tissue in the target object corresponding to the ROIs set from the designated time to sequentially following thereafter. A second memory unit stores information of the movement of the tissue for a predetermined duration.

20 Claims, 9 Drawing Sheets

U.S. PATENT DOCUMENTS

| | | |
|---|---|---|
| 2004/0111028 A1* | 6/2004 | Abe et al. ............... 600/437 |
| 2006/0173292 A1* | 8/2006 | Baba et al. ............. 600/425 |
| 2006/0173309 A1* | 8/2006 | Suzuki et al. ........... 600/437 |
| 2007/0016031 A1* | 1/2007 | Mourad et al. .......... 600/437 |
| 2007/0032725 A1* | 2/2007 | Watanabe et al. ....... 600/437 |
| 2007/0055149 A1* | 3/2007 | Suzuki et al. ........... 600/437 |
| 2007/0167809 A1* | 7/2007 | Dala-Krishna .......... 600/459 |
| 2007/0213614 A1* | 9/2007 | Suzuki et al. ........... 600/443 |
| 2008/0095417 A1* | 4/2008 | Pedrizzetti et al. ...... 382/128 |
| 2009/0143675 A1* | 6/2009 | Suzuki et al. ........... 600/438 |
| 2009/0227867 A1* | 9/2009 | Suzuki et al. ........... 600/443 |
| 2010/0036248 A1* | 2/2010 | Chouno .................. 600/443 |
| 2010/0063391 A1* | 3/2010 | Kanai et al. ............. 600/437 |
| 2010/0198072 A1* | 8/2010 | Abe et al. ............... 600/443 |
| 2011/0054314 A1 | 3/2011 | Tanigawa et al. |
| 2011/0144495 A1* | 6/2011 | Wilkening et al. ...... 600/443 |

FOREIGN PATENT DOCUMENTS

| | | |
|---|---|---|
| JP | 2003250804 | 9/2003 |
| JP | 2004077862 | 3/2004 |
| JP | 2006312072 | 11/2006 |
| JP | 2010194299 | 9/2010 |

\* cited by examiner

ULTRASOUND DIAGNOSTIC APPARATUS AND METHOD FOR TRACING MOVEMENT OF TISSUE

CROSS REFERENCE TO RELATED APPLICATIONS

This application claims the benefit of Japanese Patent Application No. 2010-241317 filed Oct. 27, 2010, which is hereby incorporated by reference in its entirety.

BACKGROUND OF THE INVENTION

The embodiments described herein relate to an ultrasound diagnostic apparatus for diagnosing blood vessel using ultrasound.

In recent years, number of patients diagnosed with circulatory condition, such as cerebral infarction and cardiac infarction, are on the rise. To prevent from such disease, it is important to detect a symptom of arteriosclerosis in its early stage and to improve a lifestyle.

To diagnose an arterial problem, Japanese unexamined publication 2002-238903A discloses an ultrasound diagnostic apparatus that measures the diameter of blood vessel using B (brightness)-mode image. Japanese unexamined publication 2002-238903A further discloses an ultrasound diagnostic apparatus for tracing the diameter of blood vessel and blood vessel wall in which an operator sets a mark for tracing in the B-mode image displayed in the monitor, and calculating a correlation of the brightness of pixel in a region of interest (ROI) that includes previously setup mark for tracing.

Unfortunately, the correlation of the brightness of pixel as described in Japanese unexamined publication 2002-238903A may alter the diameter of blood vessel or blood vessel wall depending on the image data processing. Also the ultrasound diagnostic apparatus disclosed in Japanese unexamined publication 2002-238903A displays an ultrasound image of blood vessel to the long axis direction (toward blood flowing direction) in B-mode. However, it is preferred that, the inner diameter of blood vessel and thickness of blood vessel wall to the short axis direction (cross-section direction) is displayed as well.

It is desirable that the problems described previously should be solved.

BRIEF DESCRIPTION OF THE INVENTION

A first aspect of an ultrasound diagnostic apparatus includes a transmitting and receiving unit for transmitting an ultrasound to a target object in sequence and for receiving the ultrasound as ultrasound data reflected from a certain region of the target object including a short axis direction blood vessel in sequence; a first memory unit for storing the received ultrasound data in sequence; an image generation unit for generating an ultrasound image as a sectional image of the short axis direction blood vessel based on the received ultrasound data; and a display unit for displaying the ultrasound image generated by the image generation unit. The ultrasound diagnostic apparatus further includes a region of interest setting unit for setting a plurality regions of interest on an inner wall and an outer wall of the blood vessel of the ultrasound image displayed in the display unit at designated time, wherein the region of interest is generated by ultrasound data stored in the first memory unit; a tracing unit for tracing movement of tissue in the target object corresponding to the regions of interest set for the ultrasound image at the designated time and sequentially following thereafter; and a second memory unit for storing information of the movement of the tissue in predetermined duration based on the movement of tissue traced by the tracing unit.

In a second aspect of the ultrasound diagnostic apparatus, the ultrasound image including the sectional image of the short axis direction blood vessel is a B-mode image.

In a third aspect, the tracing unit traces the movement of the tissue in the target object by using a gradient method with spatial brightness gradient.

In a fourth aspect of the ultrasound diagnostic apparatus, when a center point is set as a center of the cross section, the region of interest setting unit displays a circle centered on the center point, and sets the plurality of regions of interest on the circle.

In a fifth aspect, the region of interest setting unit displays two circles whose radii are different than each other, set a region as a region of interest which includes intersection points for radiation indices from the center point and the two circles, and displays straight lines connecting intersection points which are a part of the radiation indices.

In a sixth aspect, the region of interest setting unit sets a certain point on the two circles as other than the intersection points.

In a seventh aspect of the ultrasound diagnostic apparatus, the display unit a traced result of the movement of the tissue for a predetermined duration, based on the information of the movement of the tissue stored in the second memory unit.

In an eighth aspect, the display unit a traced result of the tissue in a radius direction from the center and reverse thereof for a predetermined duration, based on the information of the movement of the tissue stored in the second memory unit.

In a ninth aspect, the display unit a traced result of the movement of a thickness of the wall of the blood vessel in a radius direction from the center and reverse thereof for a predetermined duration, based on the information of the movement of the tissue stored in the second memory unit.

In a tenth aspect, the display unit a traced result of the movement of an inner diameter of the blood vessel in a radius direction from the center and reverse thereof for a predetermined duration, based on the information of the movement of the tissue stored in the second memory unit.

In an eleventh aspect, the display unit a traced result of the movement of an outer diameter of the blood vessel in a radius direction from the center and reverse thereof for a predetermined duration, based on the information of the movement of the tissue stored in the second memory unit.

In a twelfth aspect, the display unit a traced result of a cross-sectional area for a predetermined duration, based on the information of the movement of the tissue stored in the second memory unit.

In a thirteenth aspect, the display unit a traced result of a distance between the tissues for a predetermined duration, based on the information of the movement of the tissue stored in the second memory unit.

In a fourteenth aspect, the tracing unit traces determines that all of the region of interest is moved and displays the moved region of interest in the display unit, when the amount of movement of the plurality of regions of interest is identical and moving in the identical direction.

The ultrasound diagnostic apparatus described herein can trace a movement of a target object within the predetermined region, including the short axis direction of blood vessel, and accurately measure the movement of tissue inside the target object.

Further objects and advantages of the present invention will be apparent from the following description of the preferred embodiments of the invention as illustrated in the accompanying drawings.

DETAILED DESCRIPTION OF THE INVENTION

<Configuration of the Ultrasound Diagnostic Apparatus 100>

Figure 1:
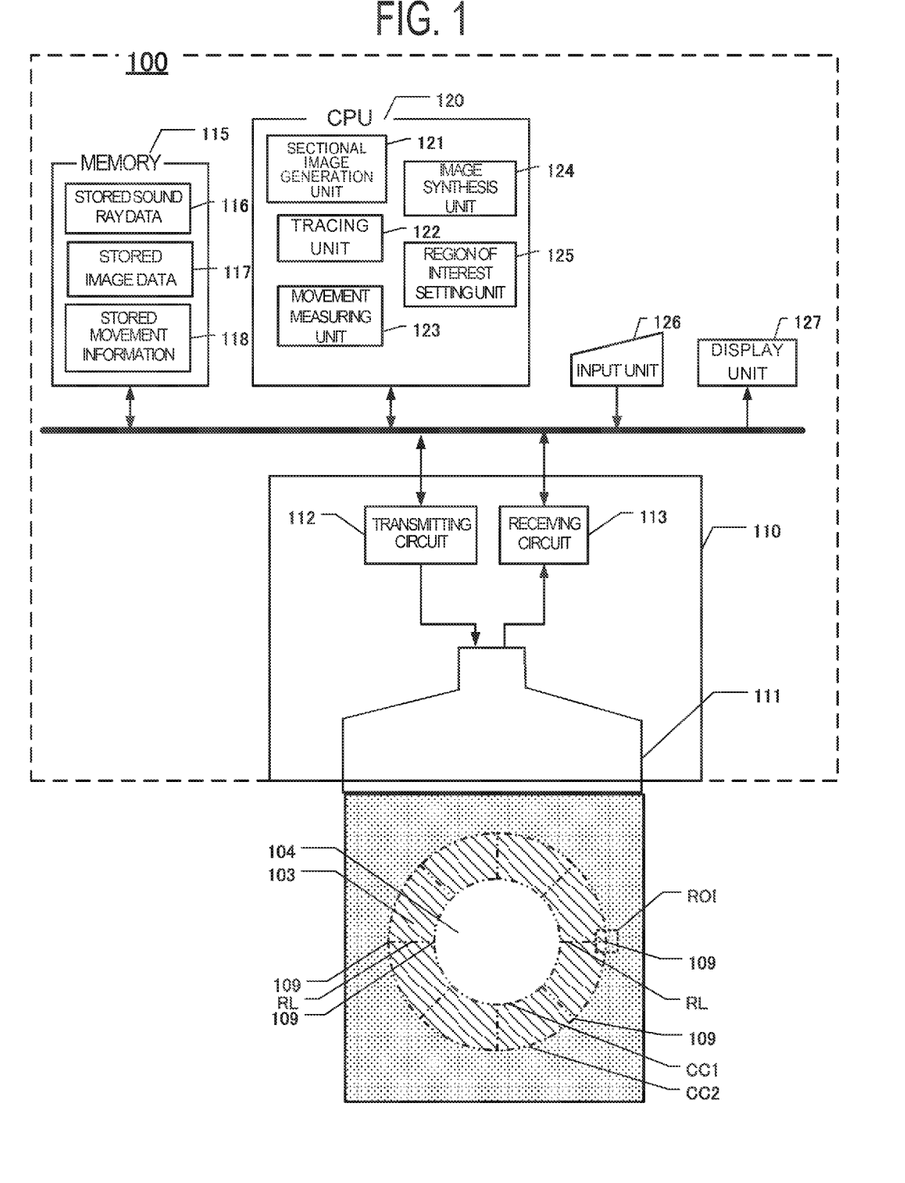
FIG. 1 is an overall diagram of an ultrasound diagnostic apparatus.

FIG. 1 is a block diagram showing the configuration of the ultrasound diagnostic apparatus 100. The ultrasound diagnostic apparatus 100 includes a transmitting and receiving unit 110, a memory 115, a CPU (central processing unit) 120, an input unit 126 for inputting through mouse or keyboard and a display unit 127 for an LCD unit, which are connected to a parallel bus.

The transmitting and receiving unit 110 includes an ultrasound probe 111, a transmitting circuit 112 and a receiving circuit 113. The ultrasound probe 111 includes a plurality of ultrasound transducers in a 1-dimensional or a 2-dimensional transducer array. The ultrasound transducers transmit an ultrasound waves based on applied driving signal to a target object, receive ultrasound echo reflected from the target object, and output a receiving signal.

The transmitting circuit 112 includes a plurality of channels, and generates a plurality of driving signals applied to each plurality of ultrasound transducers. The transmitting circuit 112 can adjust an amount of delay in the plurality of driving signals so that the ultrasound transmitted from a plurality of ultrasound transducers forms an ultrasound beam thereafter. Also, the transmitting circuit 112 can provide to the ultrasound probe 111 a plurality of driving signals, set for transmitting an ultrasound transmitted from the plurality of ultrasound transducers all at once to the image region of the target object.

The receiving circuit 113 includes a plurality of channels, receives a plurality of analog receiving signals outputted from each plurality of ultrasound transducers and amplifies thereof, and converts to digital receiving signals. Moreover, based on a received delay pattern selected from the transmitting and receiving unit 110, the receiving circuit 113 applies each delay time to a plurality of receiving signals, and processes receiving focus by adding all of the receiving signals. Due to the receiving focus processing, the sound ray data with focused ultrasound echo is formed.

In this embodiment, the ultrasound probe 111 transmits ultrasound waves from the surface of the target object to a blood vessel BV inside the target object. Also, the ultrasound probe 111 receives an ultrasound echo from the target object, including the blood vessel. The transmitting and receiving unit 110 repeats the transmission of the ultrasound waves and reception of the ultrasound echo, for outputting the sound ray data in sequence. The sound ray data processes Log compression, gain adjustment or low-pass filter processing in the receiving circuit 113, and processes an attenuation correction according to a depth of the reflecting position of ultrasound. The processed sound ray data is sequentially stored in the memory 115 through the parallel bus.

The memory 115 has capacity for storing a plurality of frames of the sound ray data 116 or a sectional image data 117, generated by an image generation unit 121.

CPU 120 includes the image generation unit 121, the tracing unit 122, the movement measuring unit 123, the image synthesis unit 124 and the region of interest setting unit 125.

The image generation unit 121 includes an image data generation function for generating sectional image data in B-mode by inputting the supplied sound ray data. The image generation unit 121 converts the B-mode sectional image data into the sectional image data that complies to the scan method of a normal television signal, performs image processing necessary for gradation process and transmits to an image synthesis unit 124 or a display unit 127, and sequentially stores into the memory 115. Also, the image generation unit 121 displays the intersection point 109, which is set in the region of interest setting unit 125, on the display unit 127.

Also, in live mode, the image generation unit 121 converts the directly supplied sound ray data into the sectional image data according to a scanning method, and in freeze mode, the image generation unit 121 converts the sectional image data 117 stored in the memory 115, into the sectional image data according to the scanning method. Moreover, during the freeze mode, when the memory 115 stores the sound ray data 116 instead of the sectional image data 117, the image generation unit 121 generates the B-mode sectional image data.

The region of interest setting unit 125 displays the intersection point 109, for designating the region of interest (ROI) in the ultrasound image using the input unit 126, such as a mouse. The operator moves a first circle CC1 and a second circle CC2, and moves the intersection point 109 for the first circle CC1, the second circle CC2 and the radiation index RL, on the display unit 127, using the mouse. Based on the signal from the intersection point 109 designated by the operator, the region of interest setting unit 125 sets the ROI that is the surrounding region including the intersection point 109 designated by the ultrasound image. The region of interest setting unit 125 automatically sets the size of the ROI. The region of interest setting unit 125 extracts the image data at the ROI. Once the ROI is set, the region of interest setting unit 125 extracts the sectional image data of the ROI, corresponding to the sectional image data 117, which is stored in the memory 115 (or the sound ray data 116 stored in the memory 115). The sectional image data extracted according to the ROI set by the region of interest setting unit 125 is supplied to the tracing unit 122.

Although, the ROI is designated in the diagram of the blood vessel of the short axis direction in the target object as shown in FIG. 1, the ROI does not always need to be designated in the display unit 127. Also, when the traced result informs that the blood vessel is moving as a whole from the tracing unit 122, as explained below, the display unit 127 can display the point 109 and the ROI to trace the movement of the blood vessel as a whole.

The tracing unit 122 traces which vector direction the ROI is moving to, from the predetermined time. To trace the ROI, a method of calculating the velocity field of the motion object in the moving image (optical flow) is used. There are many methods in an optical flow. According to an experiment, a gradient method was suitable for tracing a blood vessel wall. The gradient method is suitable for tracing minute movements and especially for tracing minute movements of the blood vessel wall. The result of the tracing unit 122 tracing the ROI is transmitted to the image synthesis unit 124, the movement measuring unit 123 and the memory 115.

The movement measuring unit 123 measures the distance of the movement of tissue at a predetermined time based on the movement of tissue in the ROI traced by the tracing unit 122. Thus, the movement measuring unit 123 can calculate the change in the diameter of the blood vessel or the elasticity of the blood vessel based on the distance of movement of tissue. The traced result measured by the movement measuring unit 123 is transmitted to the image synthesis unit 124, the memory 115 and the display unit 127. The traced result transmitted to the memory 115 is stored as movement information 118. The traced result transmitted to the display unit 127 is displayed in real-time as the total amount of movement of tissue inside the ROI.

The image synthesis unit 124 synthesizes the sectional image data supplied from the image generation unit 121, the movement information 118 traced by the tracing unit 122 and the traced result measured in the movement measurement unit 123, and synthesizes two images therewith. Image synthesis unit 124 can retrieve the sound ray data 116 or sectional image data 117, stored in the memory 115, on a necessary basis.

A diagram of blood vessel in the short axis direction inside the target object as shown in FIG. 1 is explained below.

Blood vessel consists of a blood vessel wall 103, which surrounds a blood flow region 104. In FIG. 1, sixteen intersection points 109, intersections for first circle CC1, second intersection CC2 and the radiation index RL, are found. The region of interest setting unit 125 sets the ROI to each intersection point 109. The ROI is not necessary to be displayed on the display unit 127, and in FIG. 1, one of the regions of interests ROI is shown in the dotted line. The short axis direction refers to the cross-section direction of the blood vessel.

<Method for Measuring Blood Vessel>

Figure 2:
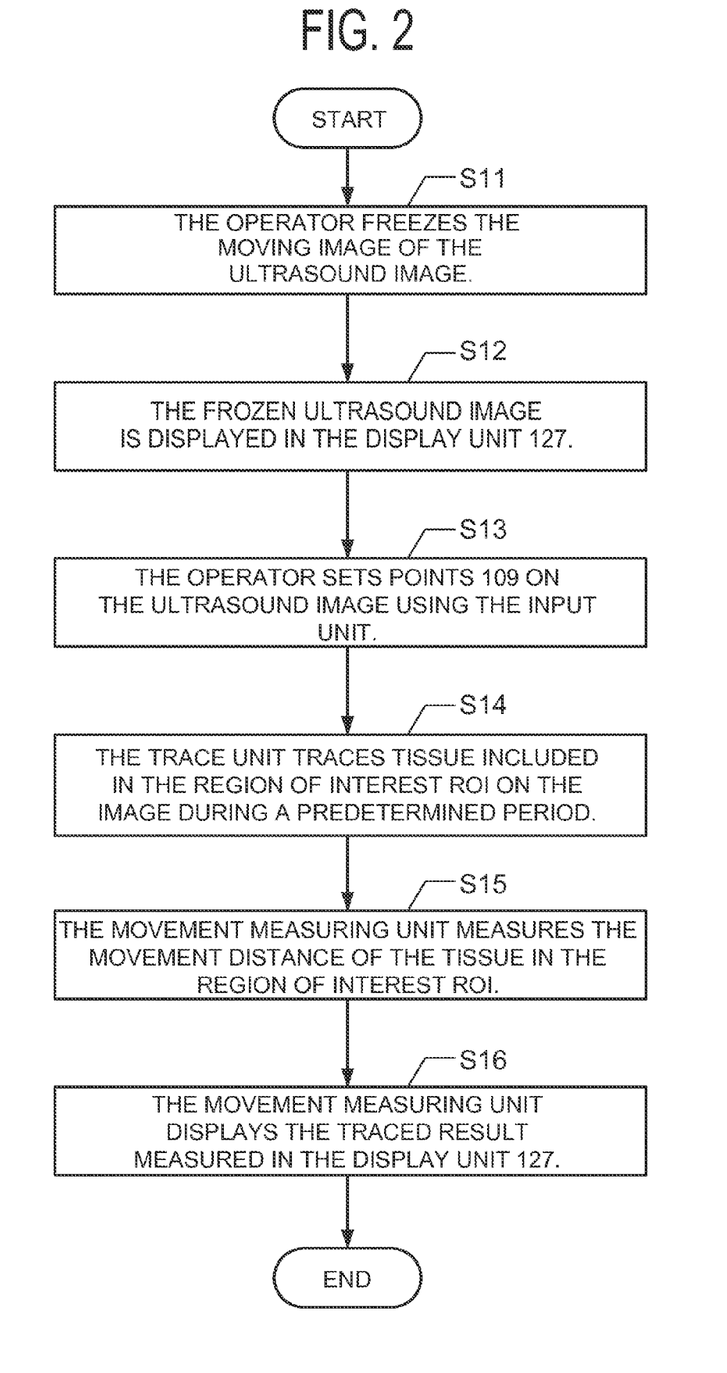
FIG. 2 is a flowchart showing the method of measuring a blood vessel.

FIG. 2 is a flow chart showing the method for measuring the blood vessel.

In step S11, the operator confirms that the moving image of the ultrasound image is stably obtained, and presses a freeze button (not described on figure).

In step S12, when the freeze button is pressed, the sound ray data 116 or the sectional image data 117 acquired during a few seconds after pressing the freeze button are stored in the memory 115, and the ultrasound image stored in the first frame is displayed in the display unit 127. The sound ray data 116 or the sectional image data 117 acquired a few seconds after pressing the freeze button can be stored in the memory 115 as well.

In step S13, the operator designates the point 109 in the ultrasound image displayed on the first frame displayed in the display unit 127 by using the input unit 126 connected by a parallel bus, such as a mouse. The region of interest setting unit 125 sets the ROI to the surrounding region, including the point 109. The operator can easily set the ROI to the blood vessel inside the target object, which is displayed in the display unit 127. In this embodiment, at least two or more ROIs should be set.

In step S14, the tracing unit 122 traces the movement of tissue, which includes at least two points of the ROIs, using frames of ultrasound images from the initial frame of the ultrasound image to the frame of the ultrasound image after the predetermined duration. The ROI is traced using the gradient method.

In step S15, the movement measuring unit 123 traces, for example, the movement of tissue included at two positions of the ROI. For example, when two regions of interest are positioned symmetrically from the center of the blood vessel on the inner wall of the blood vessel wall 103, the movement measuring unit 123 is able to understand how the inner diameter of the blood vessel is changing, in comparison to the ultrasound image of the first frame.

In step S16, the display unit 127 displays the traced result, measured by the movement measuring unit 123, in a graph for example. The display unit 127 is able to display a graph adjacent to the displayed ultrasound image, or display a graph on a separate window.

<Tracing the ROI by Gradient Method>

An optical flow method for the tracing unit 122 tracing the movement of tissue in the ROI, at step S14, is explained below. In the optical flow method, a characteristic matching method, a method for matching the characteristic of images and calculating the movement, and a gradient method, a method for calculating the movement by calculating the gradient of the contrasting density (brightness) of an image for comparing the contrasting density of the image, is used. An experiment using both the characteristic matching method and the gradient method was performed on the ultrasound image including the blood vessel displayed in the B-mode. As a result, less difference in tracing was found in the gradient method. Thereby the gradient method is one of the fastest processing and the most reliable method.

Figure 3:
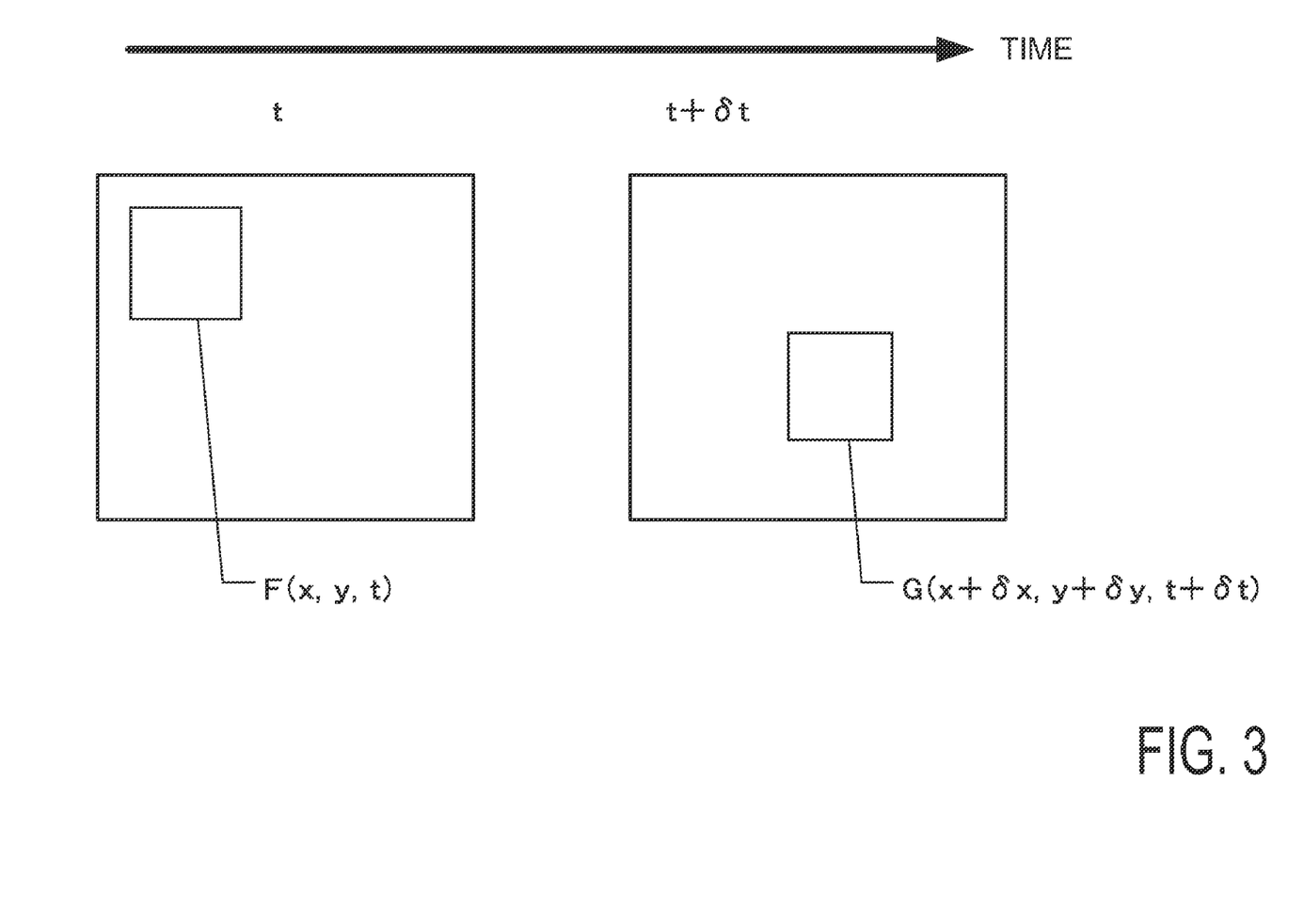
FIG. 3 is a diagram explaining the brightness gradient of the grayscale image.

As shown in FIG. 3, the contrasting density image F (p, t) includes a gradient of contrasting density (brightness gradient). The gradient method traces the movement of tissue included in the ROI by using the gradient of contrast.

As shown in FIG. 3, an image of contrasting density image "F" at time "t" (p, t) moved with even contrasting density after a minute duration (δ, t), is calculated as a contrasting density image G (p+δp, t+δt). The distance of movement is calculated using the following equation:

$$h_0 = 0, \quad h_{k+1} = h_k + \frac{\Sigma w(p)F'(p + h_k)[G(p) - F(p + h_k)]}{\Sigma w(p)F'(p + h_k)^2} \quad (\text{Eq. 1})$$

The distance of movement (vector) of tissue in the ROI is calculated by doing the iterative operation of equation 1.

In equation 1, "h" represents the distance of approximate movement, w (p) represents the weight coefficient, F (p) represents the contrasting density image before the movement, and F' (p) represents the first derivation.

The gradient method is suitable for tracing minute movements such as movement of the blood vessel wall due to the heartbeat. By tracing the movement of tissue included in the ROI using the gradient method, the minute movement of the blood vessel wall due to the heartbeat can be accurately traced.

<Setting the ROI>

Figure 4:
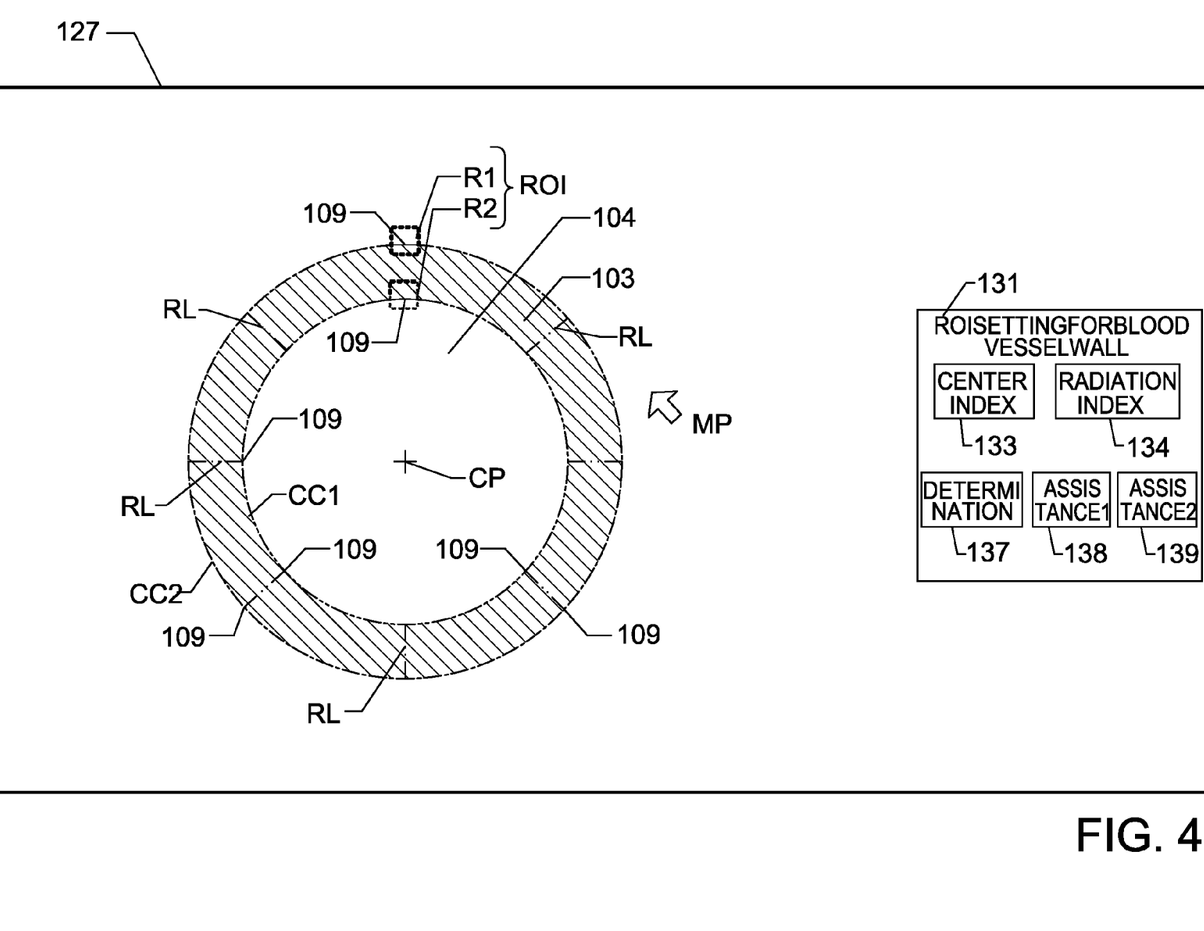
FIG. 4 is a diagram showing the setup region of interest (ROI) in the blood vessel (BV).

FIG. 4 is a diagram showing the ROI in the blood vessel extending in the short axis direction (cross-sectional direction), as displayed in the display unit 127, which was set by an operator. This is the same method as setting the ROI in the step S13 of FIG. 2.

An operator checks the ultrasound image of the initial frame displayed in the display unit 127. Then, the operator checks whether the blood vessel extending in the short axis direction is a sectional image that can easily set the ROI, and if the sectional image is an image that can easily set the ROI, the operator selects the ROI setting button (not described on figure) through the input unit 126, using the mouse pointer. The region of interest setting unit 125 (refer to FIG. 1) displays the ROI setting window 131 for the blood vessel wall, on the display unit 127.

The ROI setting window 131 for the blood vessel wall includes a center index button 133, a radiation index button 134, a determination button 137, a first assistance button 138 and a second assistance button 139.

When the center index button 133 is selected using the mouse pointer MP, a cross index CP that is the cross-shaped pointer is displayed by the display unit 127. Also, the first circle CC1, with the cross index CP located in the center, and the second circle CC2 that is a circle with a larger diameter than the first circle CC1, are displayed. The operator is able to move the cross index CP to the appropriate position, for example, the center of the cross-section of the blood vessel, using the mouse pointer MP. The first circle CC1 and the second circle CC2 moving according to the movement of the cross index CP. The operator can also move the diameter of the first circle CC1 and the second circle CC2 at appropriate positions using the mouse pointer MP.

When the radiation index button 134 is selected using the mouse pointer MP, the radiation index RL, a radiation index with a radiant shape that passes the cross index CP, is displayed by the display unit 127. When the radiation index button 134 is selected a plurality of times, a radiation index RL is displayed at an angle that does not cover the initially displayed radiation index RL. In FIG. 4, with the cross point CP as the original point, a radiation index RL extending at a 0-degrees or 180-degrees angle and the radiation index RL extending at a 90-degrees or 270-degrees angle are displayed. Also, the radiation indices RL, which passes the cross index CP and extends at 45-degrees and 225-degrees angles and at 135-degrees and 315-degrees angles are displayed as well. These radiation indices RL disappear and not displayed around the cross index CP. The ROI is rarely set around the cross index CP positioned in the center of the blood vessel in the short axis direction.

By setting the first circle CC1, the second circle CC2 and the radiation indices RL, a total of sixteen intersection points 109 are designated, as shown in FIG. 4. Region of interest setting unit 125 sets the ROI at a surrounding region, including the intersection point 109. Sixteen points of the ROIs are set, and ROI (R1, R2) is displayed at the radiation index RL at the 90-degrees angle and the intersection point 109 of the first circle CC1 and the second circle CC2 in FIG. 4. Moreover, in FIG. 4, the first circle CC1 and the second circle CC2 is drawn as a true circle. However, the shape of the circle is not restricted and it can be an oval-shaped circle.

In FIG. 4, the region of interest setting unit 125 sets the ROIs R1-R8 along the inner wall and the outer wall of blood vessel, at 0-degrees, 90-degrees, 180-degrees and 270-degrees angles by using the radiation index RL. If the operator wants to set ROIs at other arbitrary positions, an adding button for setting the ROI can be provided in the region of interest setup window 131. Once the operator completed setting the ROI, the operator clicks the determination button 137. Also, when the operator clicks the first assistance button 138 or the second assistance button 139, the radiation index that assists setting the ROI is displayed.

For example, the blood vessel as a whole may be moved because the ultrasound probe 111 and the target object are off the alignment. Therefore, when all sixteen regions of interests are moving by an identical amount in an identical direction, the tracing unit 122 does not determine that each tissue in the ROI is moving, rather it determines that the blood vessel as a whole is moving. In such a case, the display unit 127 displays the radiation index RL, the first circle CC1 and the second circle CC2 in a way that it traces the initially designated or set position. Also, the movement measuring unit 123 displays the amount of movement by subtracting the movement of the ROI from the total amount of movement. The movement measuring unit 123 averages the total movement of sixteen regions of interests.

Assisting the Setting of the ROI

First Example

Figure 5:
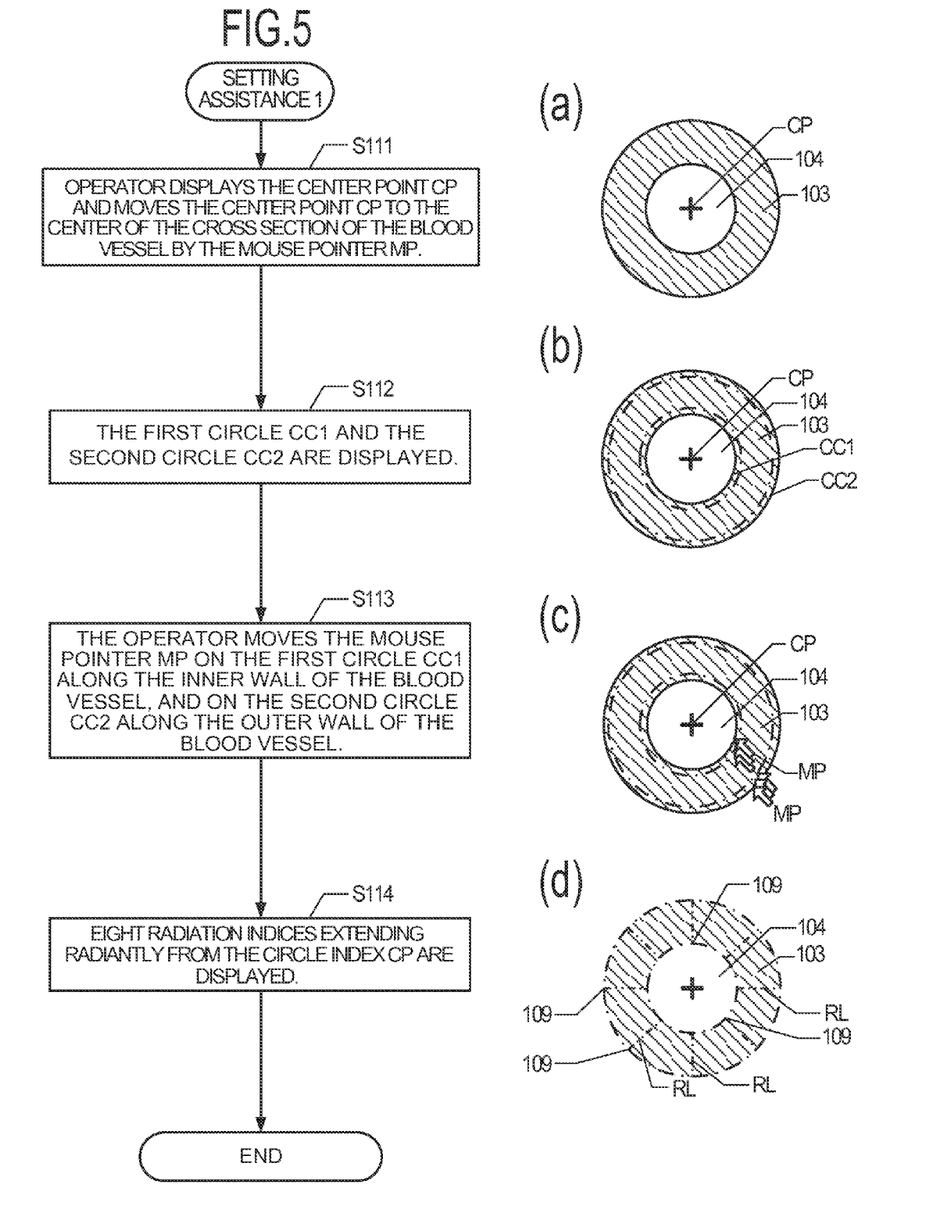
FIG. 5 is the first example of setting the ROI with assistance from the region of interest setting unit 125.

FIG. 5 is the first example of setting the ROI with assistance from the region of interest setting unit 125 (refer to FIG. 1). The flowchart on the left side corresponds to the drawings of conditions thereof, shown on the right side. FIG. 5 shows the first example of setting the ROI along the inner wall and the outer wall of the blood vessel in the horizontal direction. Therefore, R5-R8 of the ROI set in the FIG. 4 are displayed. Moreover, the horizontal direction refers to the horizontal direction of the ultrasound image displayed in the display unit 127.

In step S111, when the operator selects the first assistance button 138 (refer to FIG. 4), the region of interest setting unit 125 displays the cross index CP close to the center of the blood flow region 104. Blood flow region 104 is usually displayed in a B-mode image with dark brightness and a circle-like figure. Therefore, the region of interest setting unit 125 creates a binary image, processes the image and determines close-to-center position of the blood vessel for displaying the cross index CP. If the operator determines that cross index CP is not positioned on the center of the blood vessel, the operator can move the cross index CP to the center using the input unit 126 by moving the mouse pointer MP. Then, the operator selects the determination button 137.

In step S112, the region of interest setting unit 125 displays the first circle with the cross index CP as a center and the second circle CC2 having a larger diameter than the first circle CC1. The first circle and the second circle are concentric circles. Moreover, in FIG. 5, the first circle CC1 and the second circle CC2 are true circles. However, the shape of the circle is not limited and can be oval-shaped.

In step S113, the operator moves the mouse pointer MP on the first circle CC1 along the inner wall of the blood vessel, and on the second circle CC2 along the outer wall of the blood vessel. Then, the operator selects the determination button 137.

In step S114, the region of interest setting unit 125 displays eight radiation indices extending radiantly from the circle index CP. Radiation index RL extends between the first circle CC1 and the second circle CC2, and is displayed at 45-degrees angle apart from each other, with the cross index CP as a center. Moreover, eight radiation indices are displayed in this embodiment. However, it is not limited to eight indices and can be six radiation indices.

The first circle CC1, the second circle CC2 and sixteen intersection points 109 for eight radiation indices RL are formed in such a way, and the region of interest setting unit 125 sets the ROI in the surrounding region of the intersection point 109.

Even if the blood vessel is close to a true circle, when measuring an inner diameter of the blood vessel, if the ROI is set on a position that does not pass through the center of the blood vessel, the inner diameter cannot be measured accurately. If the blood vessel wall is deformed due to the heartbeat, setting the ROI would be difficult. Therefore, as mentioned above, the first circle CC1 and the second circle CC2, with the cross index CP as a center, and the radiation index RL, are displayed to designate the intersection point 109. Thereby a plurality of the ROIs can be easily set.

Assisting the Setting of the ROI

Second Example

Figure 6:
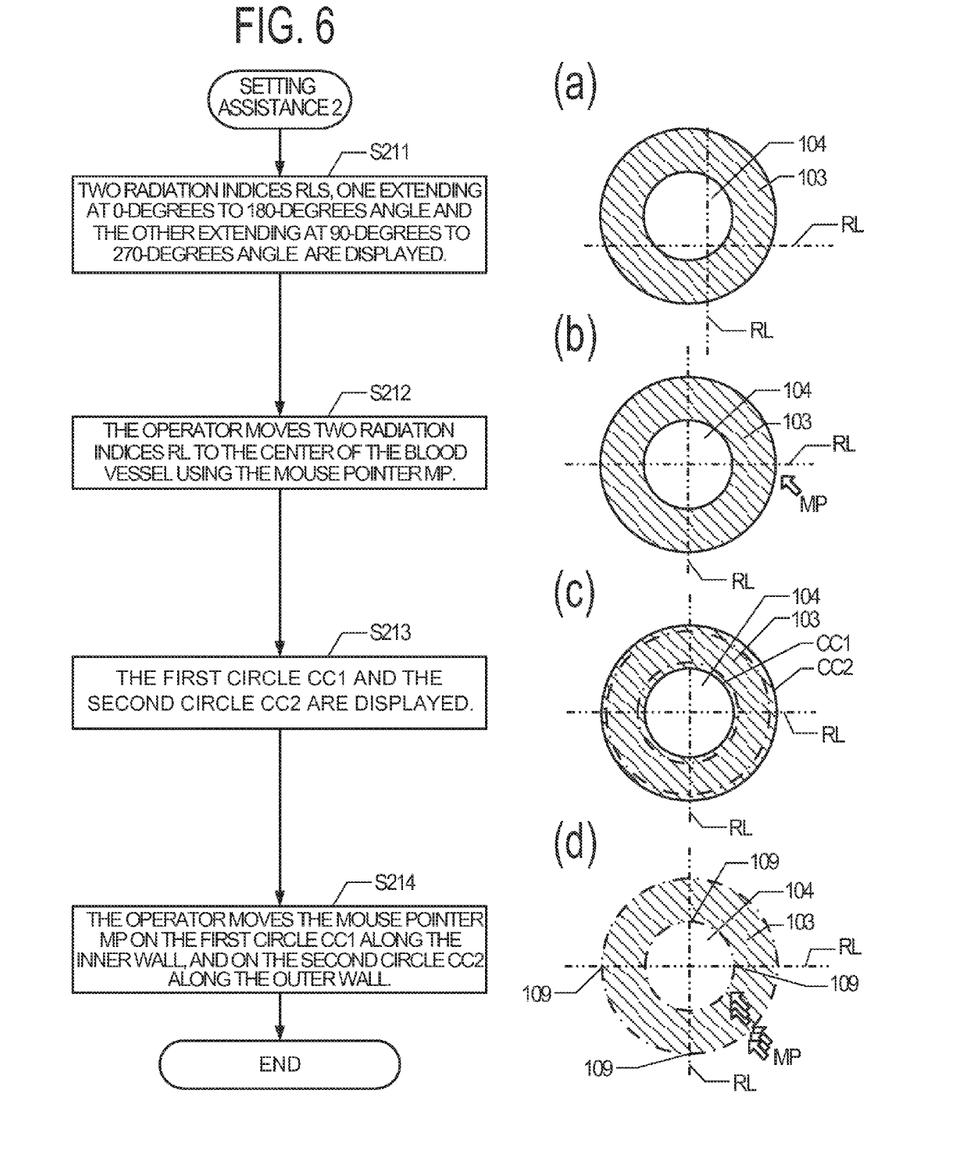
FIG. 6 is the second example of setting the ROI with assistance from the region of interest setting unit 125.

FIG. 6 is the second example of setting the ROI with assistance from the region of interest setting unit 125 (refer to FIG. 1).

The operator clicks the second assistance button 139 (refer to FIG. 2).

In step S211, the region of interest setting unit designates the radiation index RL extending at a 0-degrees to 180-degrees angle and the radiation index RL extending at a 90-degrees to 270-degrees angle.

In step S212, the operator moves two radiation indices RL to the center of the blood vessel through the input unit 126 using the mouse pointer MP. Two radiation indices RL move as a whole.

In step S213, when the operator selects the determination button 137, the region of interest setting unit 125 displays the first circle CC1 and the second circle CC2 with larger diameter than the first circle CC1, of which the common center is an intersection of two radiation indices. The first circle and the second circle are concentric circles. Moreover, in FIG. 6, the first circle CC1 and the second circle CC2 are drawn as true circles. However, the shape of the circle is not limited and can be oval-shaped.

In step S214, the operator moves the mouse pointer MP on the first circle CC1 along the inner wall of the blood vessel, and on the second circle CC2 along the outer wall of the blood vessel. Then, the operator selects the determination button 137.

When the determination button 137 is selected, the region of interest setting unit 125 sets the ROI on surrounding regions, including the first circle CC1, the second circle CC2 and the intersection point 109 of eight radiation indices RL.

In step S212, the operator moves two radiation indices RL to the center of the blood vessel. However, the region of interest setting unit 125 can display the intersection of two radiation indices close to the center of the blood vessel by image processing, as explained in the step S111 of FIG. 5. Moreover, two radiation indices RL can be radiation indices RL extending at a 45-degrees to 225-degrees angle and at a 135-degrees to 315-degrees angle, or four radiation indices can be displayed as well.

<Tracing Information of the ROI>

Figure 7:
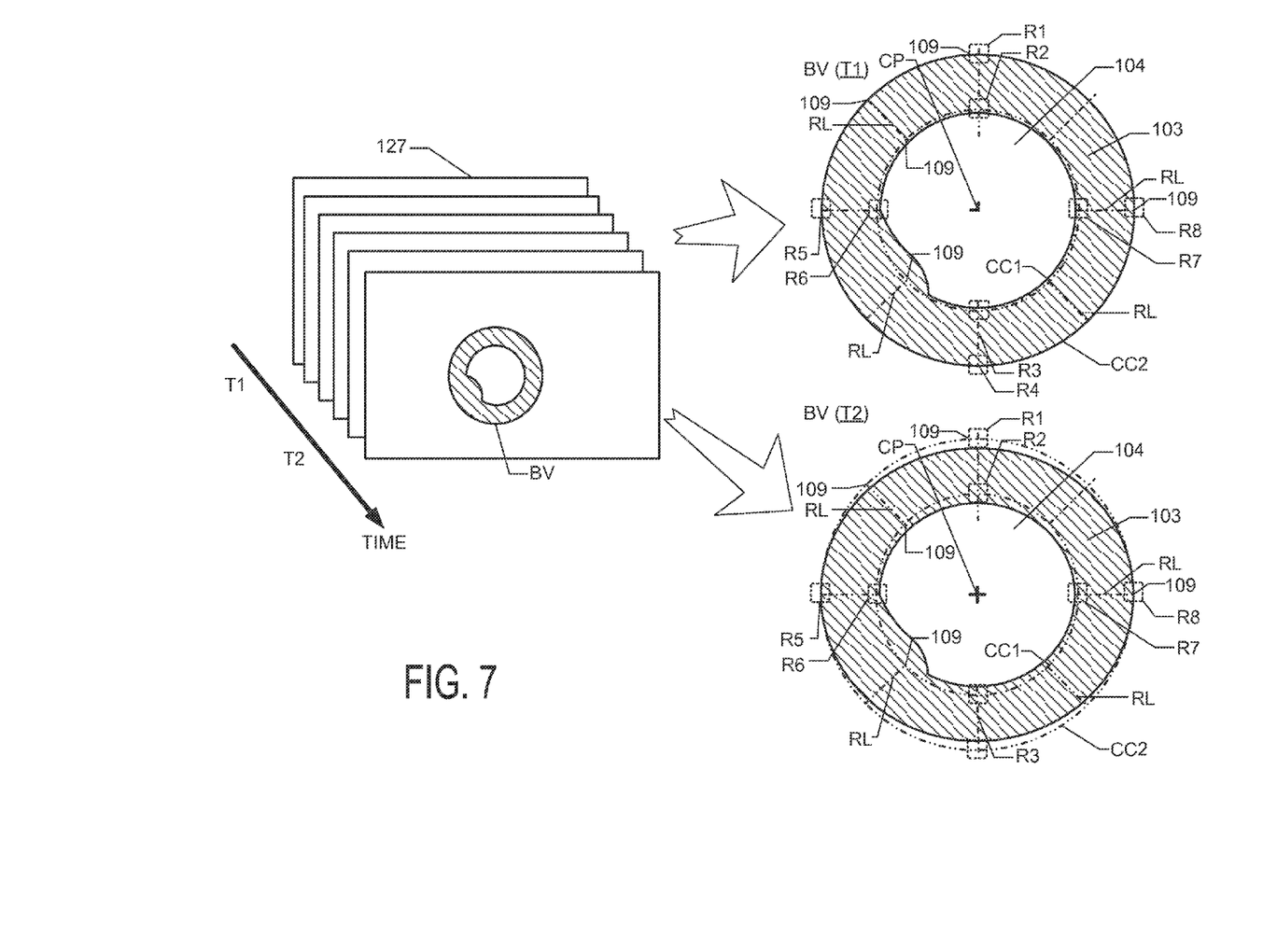
FIG. 7 shows a diagram of the first circle CC1, the second circle CC2 and eight radiation indices RL, being set in a sequence of ultrasound images displayed in the display unit 127.
Figure 9A:
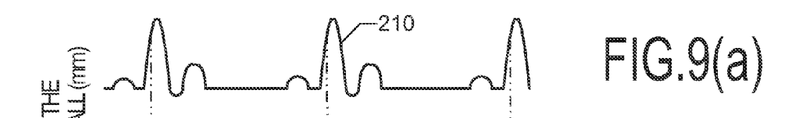
FIGS. 9(a), 9(b), 9(c), 9(d), 9(e), and 9(f) are graphs showing the thickness of the blood vessel wall and the cross-sectional area of the blood flow region 104.

FIG. 7 is a diagram showing the first circle CC1, the second circle CC2 and eight radiation indices RL, being set in a sequence of ultrasound images displayed on the display unit 127. The left side of FIG. 7 shows a plurality of frames of the ultrasound image from the predetermined time T1 to time T2 after the predetermined time has passed since time T1, and the right side of FIG. 7 are abstracts from the frame sequence taken from the ultrasound image at time T1 and the ultrasound image at time T2. Among the intersection point 109, the ROIs R1-R8, which will be explained in the FIG. 7 to FIG. 9, are displayed. The ROIs R1-R8 are drawn for further explanation and are not necessary to be always displayed.

The cross-sectional shape in the short axis direction of the blood vessel changes at time T1 and time T2 due to the heartbeat. Tissue designated with the ROIs (R1-R8) moves in the horizontal direction and the vertical direction on screen respectively. In this embodiment, eight regions of interests are set, and by selecting one ROI (R1), the movement measuring unit 123 (refer to FIG. 1) can measure the amount of movement of the ROI (R1) in the vertical direction and the horizontal direction.

Moreover, by selecting at least two ROIs among eight ROIs, the movement measuring unit 123 can measure the distance of the movement of these two ROIs. In the radiation indices RL, the ROI (R5-R8) is set accurately in the horizontal direction. Therefore, the thickness of the blood vessel wall 103 can be accurately measured based on the ROIs (R5 and R6), or based on the ROIs (R7 and R8). Moreover, the outer diameter of the blood vessel wall 103 can be accurately measured based on the ROIs (R5 and R8), or the inner diameter of the blood vessel wall 103 can be accurately measured based on the ROIs (R6 and R7).

FIGS. 8(a), 8(b), 8(c), 9(a), 9(b), 9(c), 9(d), 9(e), and 9(f) are examples of displaying the traced result measured by the movement measuring unit 123 at step S16 of FIG. 2, in graphs. These graphs are displayed based on the movement of the ROIs (R1-R8) shown in FIG. 7.

Figure 8A:
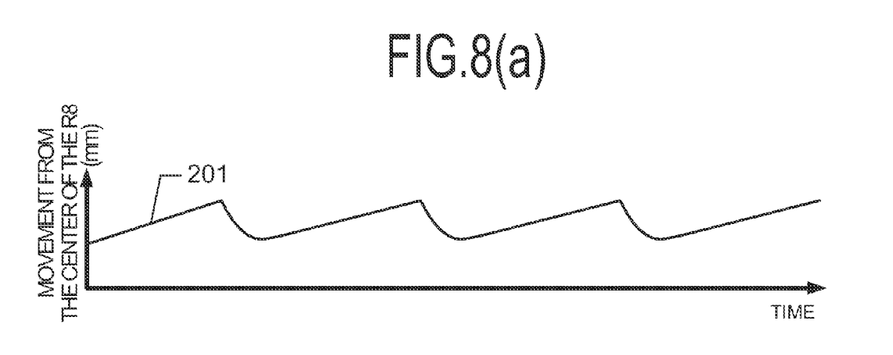
FIGS. 8(a), 8(b), and FIG. 8(c) are graphs showing the traced result of the region of interest ROI in blood vessel BV.
Figure 8B:
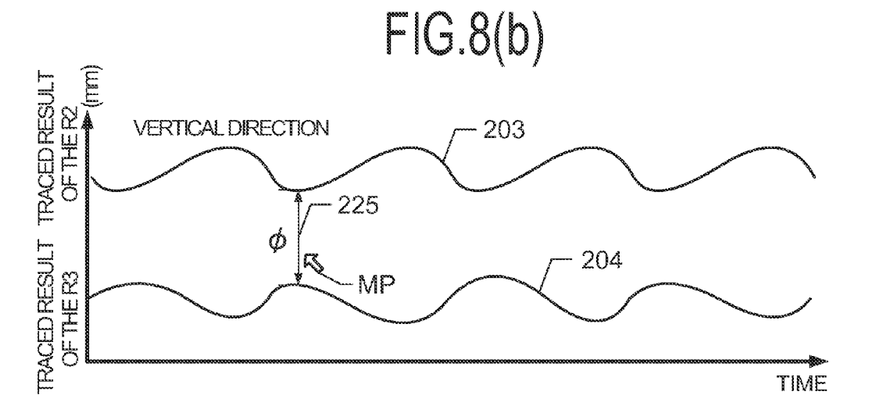
Figure 8C:
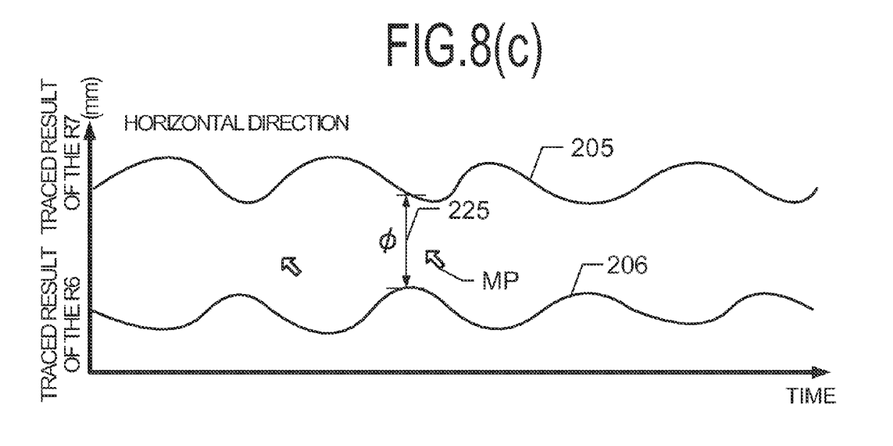

FIGS. 8(a), 8(b), and 8(c) are graphs showing the traced result of the ROI in blood vessel.

FIG. 8(a) is an example of the movement measuring unit 123 displaying the traced result of the ROI (R8) in the horizontal direction on the display unit 127. The vertical axis represents the position in millimeters (mm) and the horizontal axis represents time. The graph 201 displaying the traced result of the ROI (R8) in the vertical direction shows that the outer wall of the blood vessel wall 103 is largely moving to the radiant direction (outside to inside and inside to outside) from the center of the cross section due to the heartbeat.

FIG. 8(b) is an example of the movement measuring unit 123 displaying the traced result of the ROI (R2) and the ROI (R3) in the vertical direction on the display unit 127. ROI (R2) is the inner wall on the top side of the front wall 103 and the ROI (R3) is the inner wall on the bottom side. The graph 203 displaying the traced result of the ROI (R2) and the graph 204 displaying the traced result of the ROI (R3) show that the inner wall of the blood vessel wall 103 is moving in the vertical direction due to the heartbeat. It also displays that the difference between the graph 203 and the graph 204 is equal to the inner diameter of the blood vessel in the vertical direction. The movement measuring unit 123 can display the inner diameter of the blood vessel for an arbitrary duration by displaying the inner index 225 and the operator moving the inner index 225 using the mouse pointer MP.

FIG. 8(c) is an example of the movement measuring unit 123 displaying the traced result of the ROI (R6) and the ROI (R7) in the horizontal direction on the display unit 127. The ROI (R6) is left side inner wall of the blood vessel wall 103, and the ROI (R7) is the right side inner wall. The graph 205 of the ROI (R6) and the graph 206 of the ROI (R7) show that the inner wall of the blood vessel wall 103 is moving in the horizontal direction due to the heartbeat. Also, since the ROI (R6) and the ROI (R7) are horizontal to the blood vessel, the difference between the graph 205 and graph 206 indicates the inner diameter of blood vessel in the horizontal direction.

FIGS. 9(a), 9(b), 9(c), 9(d), 9(e), and 9(f) are graphs of one of the traced result showing the thickness of the blood vessel wall and the cross-sectional area of the blood flow region 104.

FIG. 9(a) is the graph 210 of the heartbeat signal. The heartbeat signal is displayed by placing the sensor (not described on figure) on the target object thereof.

Figure 9B:
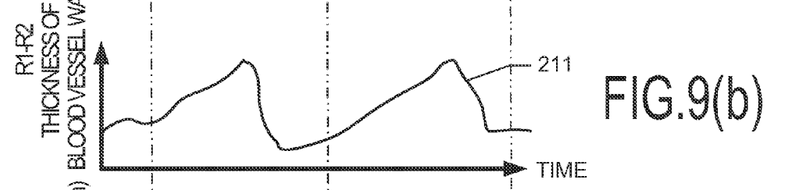

FIG. 9(b) is the graph 211 displayed on the display unit 127 in which the movement measuring unit 123 is indicating the thickness of the top side of blood vessel wall 103 by calculating the difference between the ROI (R1) and the ROI (R2) in the horizontal direction. In the graph 211, a thickness of the blood vessel wall 103 is synchronized to the graph 210 of the heartbeat signal.

Figure 9C:
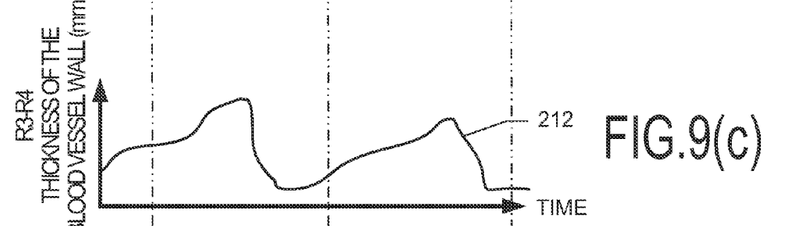

FIG. 9(c) is the graph 212 displayed on the display unit 127 in which the movement measuring unit 123 is indicating the thickness of the bottom side of blood vessel wall 103 by calculating the difference between the ROI (R3) and the ROI (R4) in the vertical direction. In the graph 212, a thickness of the blood vessel wall 103 is synchronized to the graph 210 of the heartbeat signal.

Figure 9D:
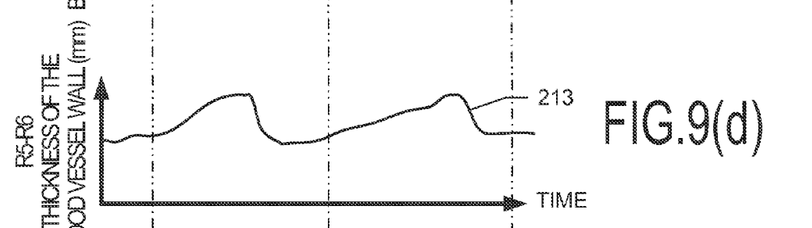
Figure 9E:
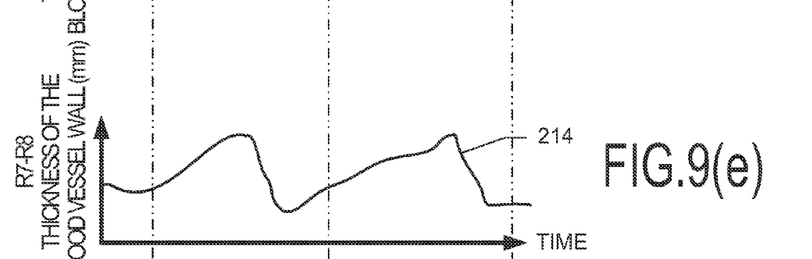

Similarly, FIG. 9(d) is the graph 213 in which the movement measuring unit 123 indicates the thickness of the blood vessel wall 103 on the left side by calculating the difference between the ROI (R5) and the ROI (R6) in the horizontal direction, and FIG. 9(e) is the graph 214 in which the movement measuring unit 123 indicates the thickness of the blood vessel wall 103 on the right by calculating the difference between the ROI (R7) and the ROI (R8) in the horizontal direction.

Figure 9F:
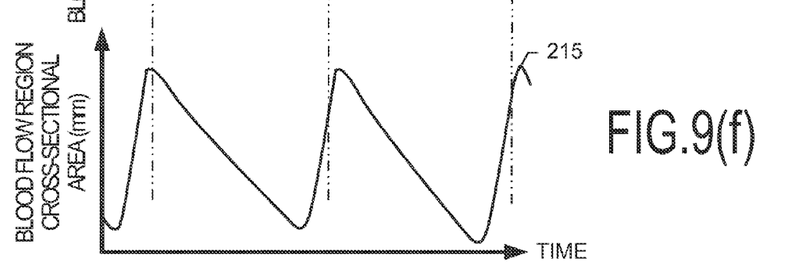

FIG. 9(f) is an example of the movement measuring unit 123 displaying the graph 215 of the cross sectional area of the blood flow region 104 on the display unit 127. In FIG. 7, the ROIs (R2, R3, R6 and R7) and four ROIs not described on this figure are set on the inner wall of the blood vessel wall 103. Therefore, the movement measuring unit 123 calculates the cross sectional area of the blood flow region 104 from the amount of the movement thereof. In FIG. 7, eight ROIs are designated on the inner wall of the blood vessel wall 103. By setting more ROIs on the inner wall of the blood vessel wall 103, a more accurate cross sectional area of the blood flow region 104 can be measured.

This embodiment described the movement measuring unit 123 displaying the change in the thickness of the blood vessel wall and the change in the inner diameter of the blood vessel. These embodiments may be carried out by means of a variety of changes, such as measuring the change in the outer diameter of the blood vessel and the cross sectional area of the blood vessel wall 103 and displaying thereof. Also, as mentioned in FIG. 9(a), when the heartbeat or the blood pressure is measured, the movement measuring unit 123 can measure the stiffness parameter or the blood vessel wall diameter direction average elasticity.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasound diagnostic apparatus comprising:
a transmitting and receiving unit configured to transmit an ultrasound wave to a target object in sequence and to receive the ultrasound wave as ultrasound data reflected from a certain region of the target object including a short axis direction blood vessel in sequence;
a first memory unit configured to store the received ultrasound data in sequence;
an image generation unit configured to generate an ultrasound image as a sectional image of the short axis direction blood vessel based on the received ultrasound data;
a display unit configured to display the ultrasound image generated by the image generation unit;
a region of interest setting unit configured to set a plurality of regions of interest on an inner wall and an outer wall of the blood vessel in the ultrasound image displayed by the display unit at a designated time, wherein the regions of interest are generated from the ultrasound data stored in the first memory unit;
a tracing unit configured to trace movement of tissue in the target object corresponding to the regions of interest set in the ultrasound image from the designated time to sequentially following thereafter; and
a second memory unit configured to store information of the movement of the tissue for a predetermined duration based on the movement of tissue traced by the tracing unit.

2. The ultrasound diagnostic apparatus according to the claim 1, wherein the ultrasound image that includes the sectional image of the short axis direction blood vessel is B-mode image.

3. The ultrasound diagnostic apparatus according to the claim 1, wherein the tracing unit is configured to trace the movement of the tissue in the target object by using a gradient method with a spatial brightness gradient.

4. The ultrasound diagnostic apparatus according to the claim 1, wherein when a center point is set as a center of a cross section, the region of interest setting unit is configured to display a circle drawn around the center point and to set the regions of interest on the circle.

5. The ultrasound diagnostic apparatus according to the claim 4, wherein the region of interest setting unit is configured to display two circles whose radii are different than each other, to set a region as a region of interest that includes intersection points for radiation indices that are lines from the center point to the two circles, and to display straight lines connecting intersection points that are a part of the radiation indices.

6. The ultrasound diagnostic apparatus according to the claim 5, wherein the region of interest setting unit is configured to set a certain point on the two circles other than at the intersection points.

7. The ultrasound diagnostic apparatus according to the claim 1, wherein the display unit is configured to display a traced result of the movement of the tissue for the predetermined duration based on the information of the movement of the tissue stored in the second memory unit.

8. The ultrasound diagnostic apparatus according to the claim 2, wherein the display unit is configured to display a traced result of the movement of the tissue for the predetermined duration based on the information of the movement of the tissue stored in the second memory unit.

9. The ultrasound diagnostic apparatus according to the claim 3, wherein the display unit is configured to display a traced result of the movement of the tissue for the predetermined duration based on the information of the movement of the tissue stored in the second memory unit.

10. The ultrasound diagnostic apparatus according to the claim 4, wherein the display unit is configured to display a traced result of the movement of the tissue for the predetermined duration based on the information of the movement of the tissue stored in the second memory unit.

11. The ultrasound diagnostic apparatus according to the claim 5, wherein the display unit is configured to display a traced result of the movement of the tissue for the predetermined duration based on the information of the movement of the tissue stored in the second memory unit.

12. The ultrasound diagnostic apparatus according to the claim 6, wherein the display unit is configured to display a traced result of the movement of the tissue for the predetermined duration based on the information of the movement of the tissue stored in the second memory unit.

13. The ultrasound diagnostic apparatus according to the claim 1, wherein the display unit is configured to display a traced result of the tissue in a radius direction from a center of a region of interest and reverse thereof for the predetermined duration based on the information of the movement of the tissue stored in the second memory unit.

14. The ultrasound diagnostic apparatus according to the claim 13, wherein the display unit is configured to display a traced result of the movement of a thickness of a wall of the blood vessel in the radius direction from the center and reverse thereof for the predetermined duration based on the information of the movement of the tissue stored in the second memory unit.

15. The ultrasound diagnostic apparatus according to the claim 13, wherein the display unit is configured to display a traced result of the movement of an inner diameter of the blood vessel in the radius direction from the center and reverse thereof for the predetermined duration based on the information of the movement of the tissue stored in the second memory unit.

16. The ultrasound diagnostic apparatus according to the claim 13, wherein the display unit is configured to display a traced result of the movement of an outer diameter of the blood vessel in the radius direction from the center and reverse thereof for the predetermined duration based on the information of the movement of the tissue stored in the second memory unit.

17. The ultrasound diagnostic apparatus according to the claim 7, wherein the display unit is configured to display a traced result of a cross-sectional area for the predetermined duration based on the information of the movement of the tissue stored in the second memory unit.

18. The ultrasound diagnostic apparatus according to the claim 1, wherein the display unit is configured to display a traced result of a distance between at least two tissues for a predetermined duration based on the information of the movement of the tissue stored in the second memory unit.

19. The ultrasound diagnostic apparatus according to the claim 1, wherein the tracing unit is configured to determine that all of the regions of interest that are displayed in the display unit are moving when an amount of movement of the regions of interest is identical and the regions of interest move in an identical direction.

20. A method for tracing movement of tissue, the method comprising:
    transmitting an ultrasound wave to a target object in sequence;
    receiving the ultrasound wave as ultrasound data reflected from a certain region of the target object including a short axis direction blood vessel in sequence;
    storing the received ultrasound data in sequence;
    generating an ultrasound image as a sectional image of the short axis direction blood vessel based on the received ultrasound data;
    displaying the ultrasound image;
    setting a plurality of regions of interest on an inner wall and an outer wall of the blood vessel in the displayed ultrasound image at a designated time;
    tracing movement of tissue in the target object corresponding to the regions of interest set in the ultrasound image from the designated time to sequentially following thereafter; and
    storing information of the movement of the tissue for a predetermined duration based on the traced movement of tissue.

* * * * *